US00PP18135P2

(12) United States Plant Patent
Vandenberg

(10) Patent No.: US PP18,135 P2
(45) Date of Patent: Oct. 23, 2007

(54) ***CHRYSANTHEMUM* PLANT NAMED 'WHITE YONEEDLE'**

(50) Latin Name: *Chrysanthemum×morifolium*
Varietal Denomination: White Yoneedle

(75) Inventor: Cornelis P. Vandenberg, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 11/417,365

(22) Filed: May 3, 2006

(51) Int. Cl.
*A01H 5/00* (2006.01)

(52) U.S. Cl. ..... Plt./288

(58) Field of Classification Search ..... Plt./287, Plt./288

See application file for complete search history.

*Primary Examiner*—Kent Bell
*Assistant Examiner*—Louanne Krawczewicz Myers
(74) *Attorney, Agent, or Firm*—C. A. Whealy

(57) ABSTRACT

A new and distinct cultivar of *Chrysanthemum* plant named 'White Yoneedle', characterized by its upright plant habit; dark green-colored foliage, freely and uniformly flowering habit; quilled decorative-type inflorescences that are about 7.7 cm in diameter; attractive white-colored quilled ray florets; strong peduncles; and good postproduction longevity.

1 Drawing Sheet

Botanical designation: *Chrysanthemum×morifolium.*
Cultivar denomination: 'White Yoneedle'.

BACKGROUND OF THE INVENTION

The present invention relates to a new and distinct cultivar of *Chrysanthemum* plant, botanically known as *Chrysanthemum×morifolium,* commercially grown as a cut flower and hereinafter referred to by the name 'White Yoneedle'.

The new *Chrysanthemum* is a product of a planned breeding program conducted by the Inventor in Salinas, Calif. and Bogota, Colombia. The objective of the program is to create and develop new cut *Chrysanthemum* cultivars having inflorescences with desirable floret coloration and good inflorescence form and substance.

The new *Chrysanthemum* originated from a cross-pollination made by the Inventor in December, 2000, in Salinas, Calif. of a proprietary *Chrysanthemum×morifolium* seedling selection identified as code number T2987, not patented, as the female, or seed, parent with a proprietary *Chrysanthemum×morifolium* seedling selection identified as code number T2392, not patented, as the male, or pollen, parent. The new *Chrysanthemum* was discovered and selected by the Inventor as a single flowering plant within the progeny of the stated cross-pollination in a controlled environment in Bogota, Colombia in June, 2002. The selection of this plant was based on its desirable ray floret color and good inflorescence form and substance.

Asexual reproduction of the new *Chrysanthemum* by terminal cuttings in a controlled environment in Bogota, Colombia since August, 2002, has shown that the unique features of this new *Chrysanthemum* are stable and reproduced true to type in successive generations.

SUMMARY OF THE INVENTION

Plants of the cultivar White Yoneedle have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'White Yoneedle'. These characteristics in combination distinguish 'White Yoneedle' as a new and distinct cultivar of *Chrysanthemum:*

1. Upright cut *Chrysanthemum* that is usually grown as a naturally spray.
2. Dark green-colored foliage.
3. Freely and uniformly flowering habit.
4. Quilled decorative-type inflorescences that are about 7.7 cm in diameter.
5. Attractive white-colored quilled ray florets.
6. Response time about 62 days.
7. Strong peduncles.
8. Good postproduction longevity with inflorescences and foliage maintaining good substance and color for about two weeks in an interior environment.

Plants of the new *Chrysanthemum* differ from plants of the female parent selection in the following characteristics:

1. Plants of the new *Chrysanthemum* flower a couple days earlier than plants of the female parent selection.
2. Plants of the new *Chrysanthemum* flower more freely than plants of the female parent selection.
3. Plants of the new *Chrysanthemum* have smaller inflorescences than plants of the female parent selection.
4. Ray florets of plants of the new *Chrysanthemum* are quilled whereas ray florets of plants of the female parent selection are not quilled.
5. Plants of the new *Chrysanthemum* and the female parent selection differ in ray floret color as developing ray florets of plants of the female parent selection are slightly cream to green in color.

Plants of the new *Chrysanthemum* differ from plants of the male parent selection in the following characteristics:

1. Plants of the new *Chrysanthemum* flower slightly later than plants of the male parent selection.
2. Plants of the new *Chrysanthemum* flower more freely than plants of the male parent selection.
3. Plants of the new *Chrysanthemum* have smaller inflorescences than plants of the male parent selection.
4. Ray florets of plants of the new *Chrysanthemum* are quilled whereas ray florets of plants of the male parent selection are not quilled.

Plants of the new *Chrysanthemum* can be compared to plants of the *Chrysanthemum* cultivar Sky, disclosed in U.S. Plant Pat. No. 15,759. In side-by-side comparisons conducted in Bogota, Colombia, plants of the new *Chrysanthemum* differed from plants of the cultivar Sky in the following characteristics:

1. Plants of the new *Chrysanthemum* were shorter than plants of the cultivar Sky.
2. Plants of the new *Chrysanthemum* flowered more freely and more uniformly than plants of the cultivar Sky.
3. Plants of the new *Chrysanthemum* had smaller inflorescences than plants of the cultivar Sky.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph at the bottom of the sheet comprises a side perspective view of a typical flowering stem of 'White Yoneedle' grown as a natural spray.

The photograph at the top of the sheet comprises a close-up view of typical inflorescences of 'White Yoneedle' grown as a natural spray.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown in Oxnard, Calif. during the winter and spring in a polyethylene-covered greenhouse and under conditions and practices which approximate those generally used in commercial *Chrysanthemum* production. Measurements and numerical values represent averages for typical flowering plants. Plants were grown as single-stem natural spray cut *Chrysanthemums*. The photographs and measurements were taken when plants were about three months old.

Botanical classification: *Chrysanthemum×morifolium* cultivar White Yoneedle.

Parentage:

*Female, or seed, parent.*—Proprietary seedling selection of *Chrysanthemum×morifolium* identified as code number T2987, not patented.

*Male, or pollen, parent.*—Proprietary seedling selection of *Chrysanthemum×morifolium* identified as code number T2392, not patented.

Propagation:

*Type.*—Terminal vegetative cuttings.

*Time to initiate roots.*—About ten to 14 days with soil temperatures of about 18° C. to 21° C.

*Root description.*—Fine, fibrous; white in color.

*Rooting habit.*—Freely branching.

Plant description:

*Appearance.*—Herbaceous decorative-type cut flower that is typically grown as a natural spray.

*Flowering stem description.*—Aspect: Erect. Length: About 112 cm. Diameter: About 5 mm. Internode length: About 3.7 cm. Texture: Pubescent; longitudinally ridged. Color: 146A.

*Foliage description.*—Arrangement: Alternate; simple. Length: About 10 cm. Width: About 5.2 cm. Apex: Acuminate to mucronate. Base: Attenuate. Margin: Palmately lobed; sinuses mostly parallel. Texture, upper and lower surfaces: Pubescent; veins prominent on lower surface. Color: Developing foliage, upper surface: Darker than 147A. Developing foliage, lower surface: 146A. Fully expanded foliage, upper surface: 147A; venation, 146C. Fully expanded foliage, lower surface: Slightly darker than 147B; venation, 146D. Petiole: Length: About 2 cm. Diameter: About 2.5 mm. Texture, upper and lower surfaces: Pubescent. Color, upper and lower surfaces: 146B.

Inflorescence description:

*Appearance.*—Decorative-type inflorescence form with quill-shaped ray florets. Inflorescences borne on terminals, arising from leaf axils. Ray and disc florets develop acropetally on a capitulum. Uniformly flowering. Inflorescences not fragrant.

*Flowering response.*—Under natural conditions, plants flower in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about 62 days later when grown as a natural spray.

*Postproduction longevity.*—In an interior environment, inflorescences and foliage will maintain good color and substance for about two weeks in an interior environment.

*Quantity of inflorescences.*—Freely flowering habit, about 16 to 17 inflorescences per stem develop.

*Spray width.*—About 14 cm.

*Inflorescence size.*—Diameter: About 7.7 cm. Depth (height): About 4 cm. Disc diameter: About 1 cm. Receptacle diameter: About 2.3 cm. Receptacle height: About 7 mm.

*Inflorescence buds.*—Shape: Ovate. Height: About 1.6 cm. Diameter: About 1.2 cm. Color: 155A.

*Ray florets.*—Shape: Quilled. Surface: Mostly flat. Aspect: Initially upright; when mature, about 45° from perpendicular to the peduncle. Length: About 4.3 cm. Width: About 3 mm. Apex: Emarginate. Base: Fused. Margin: Entire. Texture: Smooth, glabrous; longitudinally ridged. Number of ray florets per inflorescence: About 160 arranged in numerous rows. Color: When opening, upper surface: 155B. When opening, lower surface: 155A. Fully opened, upper and lower surfaces: 155D.

*Disc florets.*—Shape: Tubular, elongated. Length: About 6 mm. Diameter, apex: About 1.5 mm. Diameter, base: About 1 mm. Number of disc florets per inflorescence: About 94. Color: Immature: Close to 144A. Mature: Apex: Close to 12A. Mid-section: Close to 14B. Base: Close to 145D.

*Phyllaries.*—Quantity per inflorescence/arrangement: About 22 arranged in about three whorls. Length: About 1 cm. Width: About 4 mm. Shape: Deltoid. Apex: Acute. Base: Truncate. Margin: Entire. Texture, upper surface: Smooth, glabrous. Texture, lower surface: Pubescent. Color, upper surface: Close to 146A. Color, lower surface: Close to 147B.

*Peduncles.*—Length: First peduncle: About 10.2 cm. Fourth peduncle: About 13 cm. Seventh peduncle: About 16.3 cm. Diameter: About 2 mm. Angle: About 30° to 35° from vertical. Strength: Strong. Texture: Pubescent; longitudinally ridged. Color: Close to 146B.

*Reproductive organs.*—Androecium: Present on disc florets only. Anther shape: Oblong. Anther length: About 1.5 mm. Anther color: Close to 14B. Amount of pollen: Scarce. Pollen color: 14B. Gynoecium: Present on both ray and disc florets. Pistil length: About 6 mm. Stigma shape: Bi-parted. Stigma color: 12A. Style length: About 4 mm. Style color: 145C. Ovary color: 157A.

*Seed/fruit.*—Seed and fruit production has not been observed.

Disease/pest resistance: Resistance to pathogens and pests common to *Chrysanthemums* has not been observed on plants grown under commercial conditions.

Temperature tolerance: Plants of the new *Chrysanthemum* have demonstrated good tolerance to low temperatures of about 4° C. and high temperatures of about 35° C.

It is claimed:

1. A new and distinct *Chrysanthemum* plant named 'White Yoneedle' as illustrated and described.

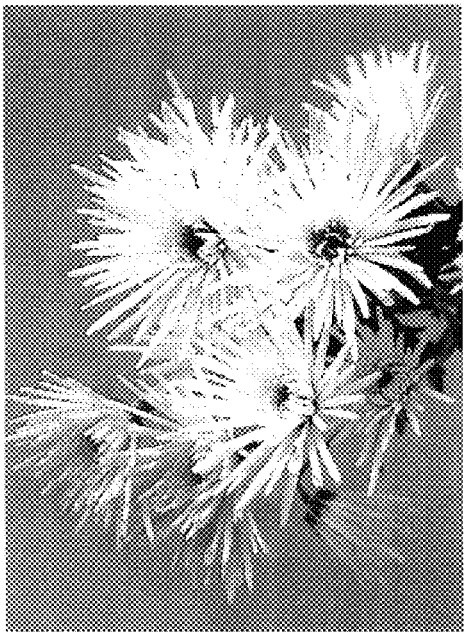
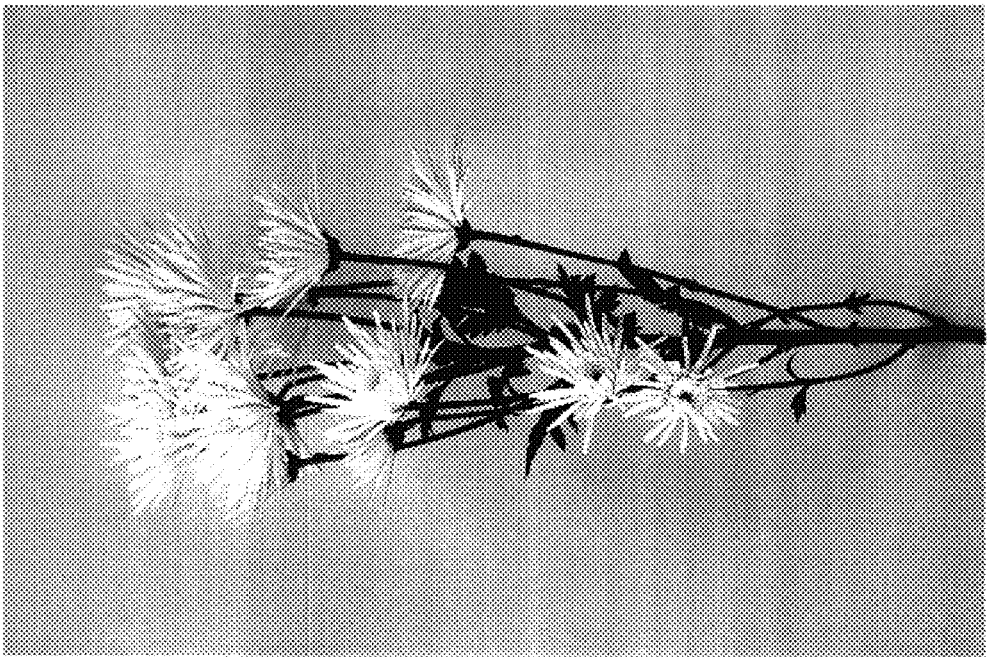

* * * * *